US006774990B2

(12) United States Patent
Liang et al.

(10) Patent No.: US 6,774,990 B2
(45) Date of Patent: Aug. 10, 2004

(54) METHOD TO INSPECT PATTERNS WITH HIGH RESOLUTION PHOTOEMISSION

(75) Inventors: Ted Liang, Sunnyvale, CA (US); Alan R. Stivers, Palo Alto, CA (US); Edita Tejnil, San Carlos, CA (US)

(73) Assignee: Intel Corporation, Santa Clara, CA (US)

( * ) Notice: Subject to any disclaimer, the term of this patent is extended or adjusted under 35 U.S.C. 154(b) by 0 days.

(21) Appl. No.: 10/226,590

(22) Filed: Aug. 23, 2002

(65) Prior Publication Data

US 2004/0036862 A1 Feb. 26, 2004

(51) Int. Cl.[7] .............................................. G01N 21/00
(52) U.S. Cl. ............................... 356/237.2; 250/492.2; 250/492.22
(58) Field of Search ........................... 356/237.1, 237.2, 356/237.3, 237.4, 237.5, 237.6; 250/492.2, 492.22, 492.24, 398; 324/158 R, 158 D, 73.1

(56) References Cited

U.S. PATENT DOCUMENTS

| 4,626,101 | A | | 12/1986 | Ogawa et al. |
| 4,694,170 | A | * | 9/1987 | Slodzian et al. ............ 250/309 |
| 4,843,329 | A | * | 6/1989 | Beha et al. ............... 250/358.1 |
| 5,118,952 | A | * | 6/1992 | Sakamoto et al. ......... 250/492.2 |
| 5,122,737 | A | * | 6/1992 | Clauberg ..................... 324/767 |
| 5,150,043 | A | | 9/1992 | Flesner |
| 6,048,745 | A | | 4/2000 | Landers et al. |
| 6,172,363 | B1 | | 1/2001 | Shinada et al. |
| 6,215,128 | B1 | * | 4/2001 | Mankos et al. ......... 250/492.24 |
| 6,291,833 | B2 | | 9/2001 | Landers et al. |

OTHER PUBLICATIONS

R.H. Watts et al., "Measuring ultrashort laser pulses in the time–frequency domain using frequency–resolved optical gating", Review of Scientific Instruments, vol. 68, No. 9, (1997) pp. 3464–3476.

David E. Seeger, "Electron–Beam, X–Ray, EUV, and Ion–Beam Submicrometer Lithographies for Manufacturing VI", Int'l. Society for Optical Engineering, SPIE vol. 2723, 11–13 Mar. 1996, pp. 211–220.

* cited by examiner

Primary Examiner—Michael P. Stafila
Assistant Examiner—Sang H. Nguyen
(74) Attorney, Agent, or Firm—Fish & Richardson P.C.

(57) ABSTRACT

Inspecting a patterned surface using photoemission of electrons includes selecting materials of the patterned surface, selecting a light source to produce a difference in yield of photoelectrons from the materials, applying the light from the light source to the patterned surface, detecting the emission of photoelectrons from the patterned surface, and inspecting the patterned surface based on the detected photoelectron emissions.

85 Claims, 7 Drawing Sheets

METHOD TO INSPECT PATTERNS WITH HIGH RESOLUTION PHOTOEMISSION

BACKGROUND

Inspection of patterns on both semiconductor wafers and masks used in lithographic processing is extremely important to ensure successful device fabrication. Even minute irregularities in a pattern can result in a nonfunctioning device.

Optical inspection is commonly used for inspection of masks and semiconductor wafers. Optical inspection systems focus ultraviolet (UV) or deep ultraviolet (DUV) light onto the pattern surface and collect the transmitted or reflected light signals to form an image of the pattern. Shorter wavelength light sources allow resolution of smaller feature sizes than longer wavelength light sources. However, light sources of wavelengths below 200 nm that also provide the necessary power and repetition rate for use in an inspection system are not readily available. Therefore, the minimum resolvable feature size of such systems typically is limited to approximately 100 nm for defects. Some optical inspection using high numerical aperture (NA) optics and/or improved inspection algorithms.

Scanning electron beam inspection is another inspection technology. Scanning electron beam inspection systems focus electron beams from an electron gun and scan the beams across the surface of a pattern. An image is formed by collecting secondary electrons emitted from the surface. The use of reflected electrons (rather than photons) allows electron beam inspection systems to resolve significantly smaller pattern feature sizes than are resolved by optical inspection systems. For example, some scanning electron inspection systems resolve minimum pattern feature sizes on the order of 50 nm for primary features and defects. However, electron beam inspection systems generally are much slower than optical systems and, as a result, electron beam inspection typically is used in wafer sampling rather than in the 100% wafer inspection needed during wafer processing.

DETAILED DESCRIPTION

Photoemission is the release of electrons from a usually solid material by means of energy supplied by incidence of photons. Whether a material exhibits photoemission depends on the intrinsic properties of the material and the frequency of the light directed at the material. Each material has its own photoelectron intensity curve that describes its photoelectron response to various frequencies of light.

Figure 1A:
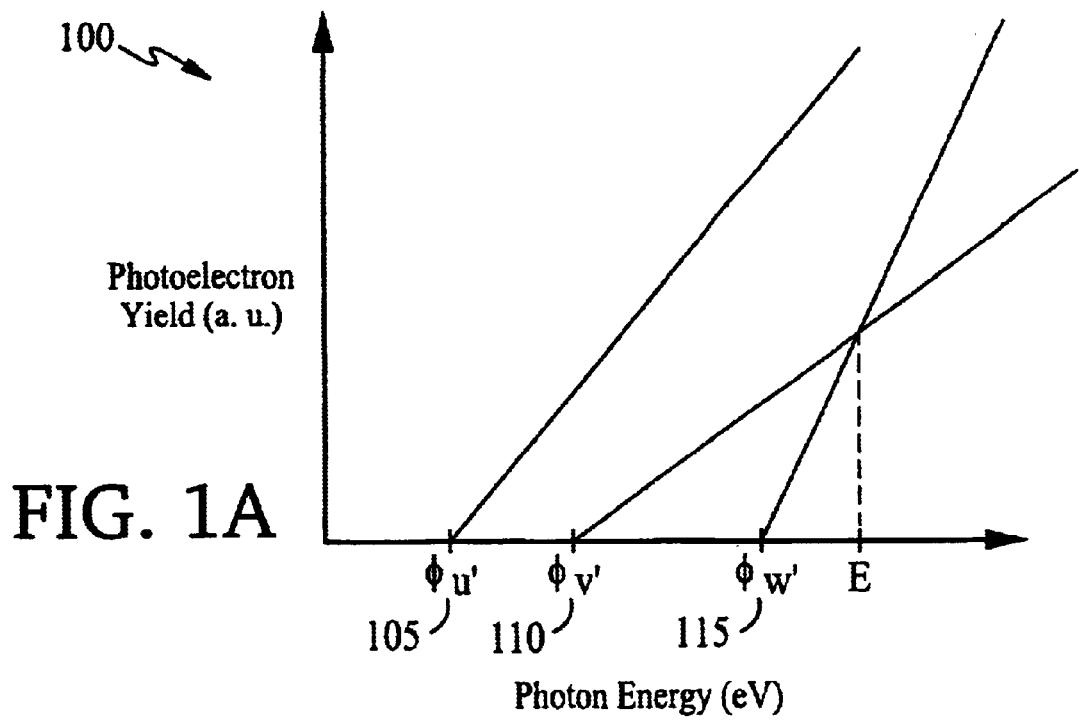
FIGS. 1A and 1B are exemplary graphs of the intensity of emitted photoelectrons as a function of the photon energy of a light source.

FIG. 1A shows a graph 100 of the intensity of emitted photoelectrons from a material as a function of the photon energy of a light source that is directed at that material. The photoelectron intensity curves of three materials u', v', and w' are shown. The work functions (i.e., photoemission threshold or electron affinity) of these three materials are represented by the intercepts of their respective photoelectron intensity curves with the photon energy axis. The work functions are labeled $\Phi u'$ 105, $\Phi v'$ 110, and $\Phi w'$ 115. The photoelectron intensity curves may be approximated as straight lines for photon energies up to about 5–10 eV above the work function.

The work function of a given material represents the minimum energy that a photon impinging on that material must have in order to cause a photoelectron to be emitted from the material. The energy of a photon is dependent on the frequency of the light source that generates the photon. Specifically, Ephoton=hv, where Ephoton is the energy of the photon, h is Planck's constant (i.e., a fundamental constant of nature with the value 6.63×10^(−34), and v is the frequency of the light source. The frequency of the light source also may be expressed in terms of the wavelength of the light source, for example, v=c/lambda, where c is the speed of light and lambda is the wavelength of the light source.

Due to the effects of quantum efficiency, which differ from one material to another, the photoelectron intensity curves of different materials exhibit different slopes and, therefore, may cross over each other. For example, FIG. 1A shows that the photoelectron emission intensity of material v' is greater than that of material w' for light sources with photon energies below E (i.e., the cross over energy) but less than that of material w' for light sources with photon energies above E. For ease of discussion, however, the following description focuses on a photon energy range in which no cross-over of photoelectron intensity curves occurs. Nevertheless, the described techniques and systems are equally applicable to inspecting patterns using light sources with photon energies near or around material cross over energies.

Figure 1B:
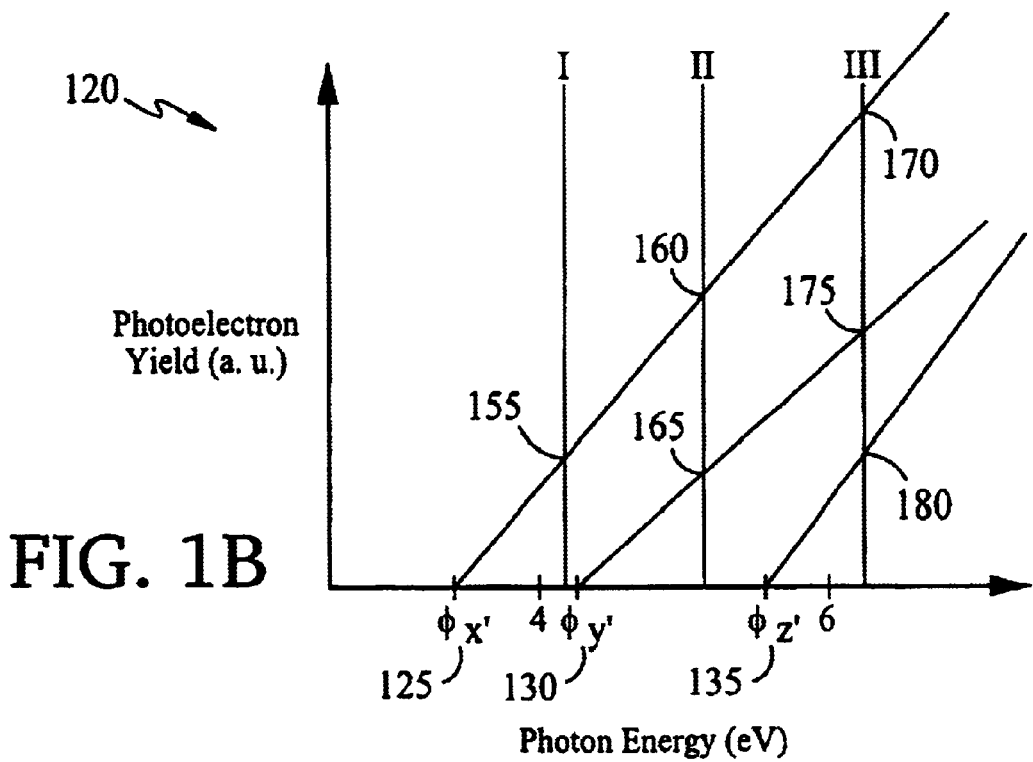

FIG. 1B shows a graph 120 similar to the graph 100 except that photoelectron intensity curves of three different materials x', y' and z' are shown. The graph 120 shows a photon energy range in which none of the photoelectron intensity curves cross over each other. The work functions of the three materials are labeled $\Phi x'$ 125, $\Phi y'$ 130, and $\Phi z'$ 135.

The photon energies of three light sources of increasing frequency I, II, and III are shown,on graph 120 as vertical lines. The photon energy of light source I is greater than the work function $\Phi x'$ 125, slightly less than the work function Φy' 130, and less than the work function Φz' 135. Therefore, when light source I is directed at the three materials x', y', and z', only material x' emits photoelectrons. The photon energy of light source I is not high enough to cause materials y' and z' to emit photoelectrons. The photoelectron intensity of the emitted electrons from material x' is the point 155 on the photoelectron intensity curve of x' that corresponds to the photon energy of the light source I.

The photon energy of light source II is greater than both the work functions Φx' 125 and Φy' 130 but less than the work function Φz' 135. Therefore, when light source II is directed at the three materials x', y', and z', only materials x' and y' will emit photoelectrons. The photon energy of light source II is not high enough to cause material z' to emit photoelectrons. The intensities of the photoelectrons emitted from materials x' and y' are the points 160 and 165 on their respective photoelectron intensity curves corresponding to the photon energy of light source II. More photoelectrons will be emitted from material x' than material y' because of the higher photoelectron intensity of material x' as compared to that of material y'.

The photon energy of light source III is greater than all three work functions Φx' 125, Φy' 130, and Φz' 135. Therefore, when light source III is directed at the three materials x', y', and z', all three of the materials emit photoelectrons. The intensities of the emitted electrons, however, are different for each material. Specifically, material x' emits more electrons than both material y' and z', and material y' emits more electrons than material z'. The photoelectron intensities of the three materials x', y', and z' are the points 170, 175, and 180 on their respective photoelectron curves corresponding to the photon energy of light source III. The photoelectron intensity of material x' is greater than that of material y' which is, in turn, greater than that of material z'.

Materials that are transparent to the light used will not emit photoelectrons. The light will be transmitted to the material below, if any. Electrons could be internally photo-emitted from that material to the transparent material above. The transparent material is usually thick enough (>20 nm) to prevent any internally photoemitted electrons from reaching the vacuum and being detected.

FIG. 2 shows a cross-section of a patterned surface 200. The patterned surface 200 includes a substrate 205, a patterned layer 210, and a patterned layer 215. The patterned layer 215 is positioned on the patterned layer 210, and the patterned layer 210 is positioned on the substrate 205. The substrate 205, the patterned layer 210, and the patterned layer 215 are composed of materials x', y', and z', respectively. The patterned surface 200 includes exposed portions of the substrate 205, the patterned layer 210, and the patterned layer 215 (i.e., portions that are visible when viewed from a direction substantially perpendicular to the plane of the substrate 205.) The patterned surface 200 is presented for purposes of illustration and is not meant to limit the number of layers, their combination, and/or the configuration of patterns described.

Inspection of the patterned surface 200 may be implemented by directing a light of a predetermined frequency at the patterned surface 200 and collecting the electrons emitted from the surface 200. The collected electrons may be used to create a display image of the patterned surface. The display image may be used to inspect the surface 200. For example, a photoelectron inspection system may include three different light sources: light source I, light source II, and light source III. For simplicity, the following description assumes that the number of photons per second per area generated by each light source is the same so that the only difference between the light sources is the energy imparted per photon.

Figure 2A:
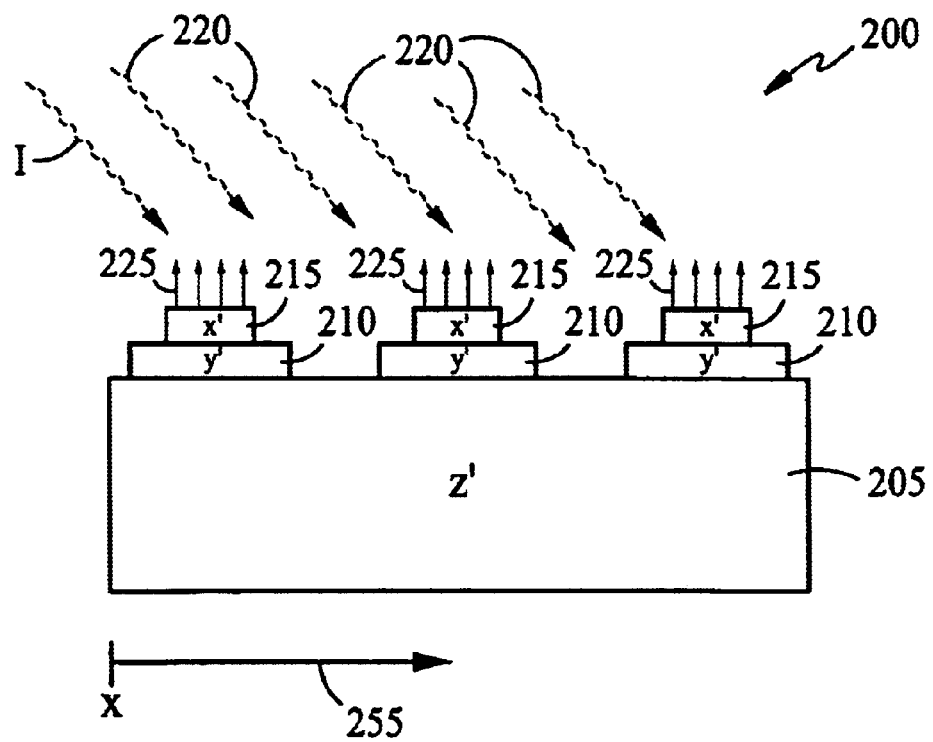
FIGS. 2A and 2B illustrate an example of inspection of a patterned surface (FIG. 2A) and a corresponding photoelectron yield graph (FIG. 2B) when the inspection system employs a given light source.
Figure 2B:
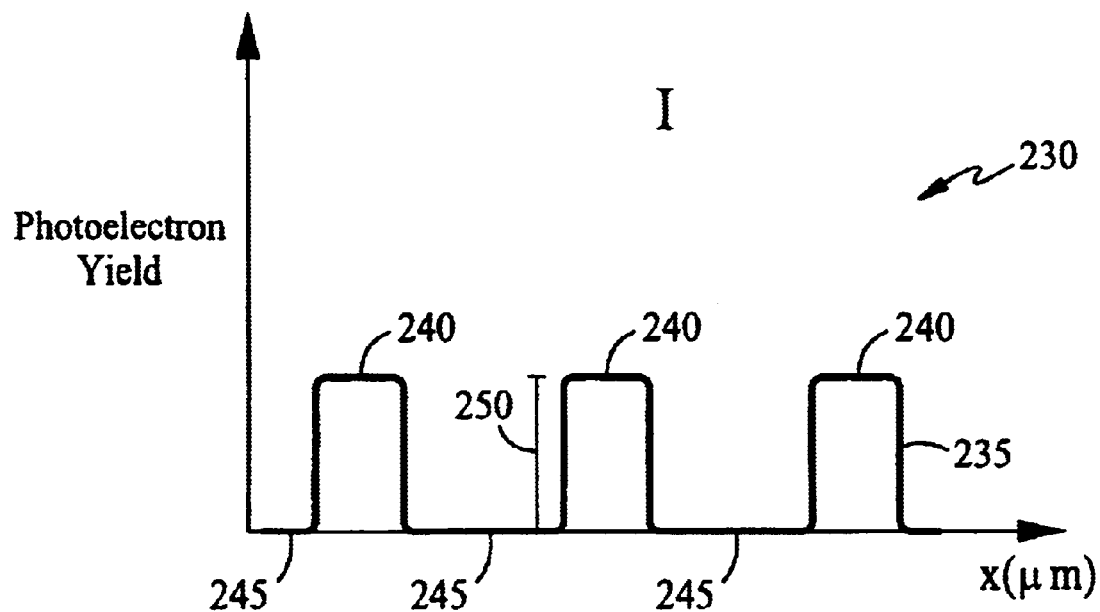

FIGS. 2A and 2B show the inspection of patterned surface 200 using light source I. As shown in FIG. 2A, photons 220 from light source I are directed at the patterned surface 200. The photons 220 impinge upon the exposed portions of the substrate 205, the patterned layer 210, and the patterned layer 215. The photons 220 have enough energy to cause electrons to be emitted from the exposed portions of the patterned layer 215 but do not have enough energy to cause electrons to be emitted from the exposed portions of the substrate 205 and the patterned layer 210. This is consistent with FIG. 1 in which the photon energy of light source I is less than both the work function Φy' 130 of the patterned layer 210 and the work function Φz' 135 of the substrate 205. The emitted electrons 225 may be represented as vertical arrows extending from the surface of the exposed portions of the patterned layer 215.

The amount of emitted electrons that may be collected from the patterned surface 200 along an x-axis 255 is shown in the photoelectron yield graph 230 of FIG. 2B. The x-axis is defined as the axis parallel to the cross-sectional surface of the substrate 205 as shown in FIG. 2A.

The yield of photoelectrons emitted from the patterned surface 200 is represented by a yield curve 235. In this example, the yield curve 235 exhibits peaks 240 that correspond to the exposed portions of the patterned layer 215. The yield curve 235 slopes down steeply from the peaks 240 to troughs 245 at the points on the x-axis corresponding to the boundaries of the exposed portions of the patterned layer 215. The peaks 240 have a maximum yield proportional to the photoelectron intensity 155 of the material x'. Similarly, the troughs 245 have a minimum yield of approximately zero because no electrons are emitted from the patterned layer 210 and the substrate 205.

The difference 250 between the maximum yield of the peaks 240 of the yield curve 235 and the minimum yield of the troughs 245 is directly correlated to the image contrast that may be achieved when the photoelectrons emitted from the surface are collected and used to create an image of the surface. In particular, the image contrast increases with the difference between the maximum yield and the minimum yield. In the example shown in FIGS. 2A and 2B, a photoelectron inspection system can generate a high quality image of the patterned layer 215 because the difference between the maximum and minimum yields of the yield curve is large enough to produce a high image contrast.

As can be seen in FIGS. 2A and 2B, neither the patterned layer 210 nor the substrate 205 may be directly imaged by a photoelectron inspection system using light source I. The patterned layer 210 and the substrate 205 do not emit electrons in response to light source I, and, therefore, no electrons from these layers may be detected for imaging purposes using light source I.

Figure 3A:
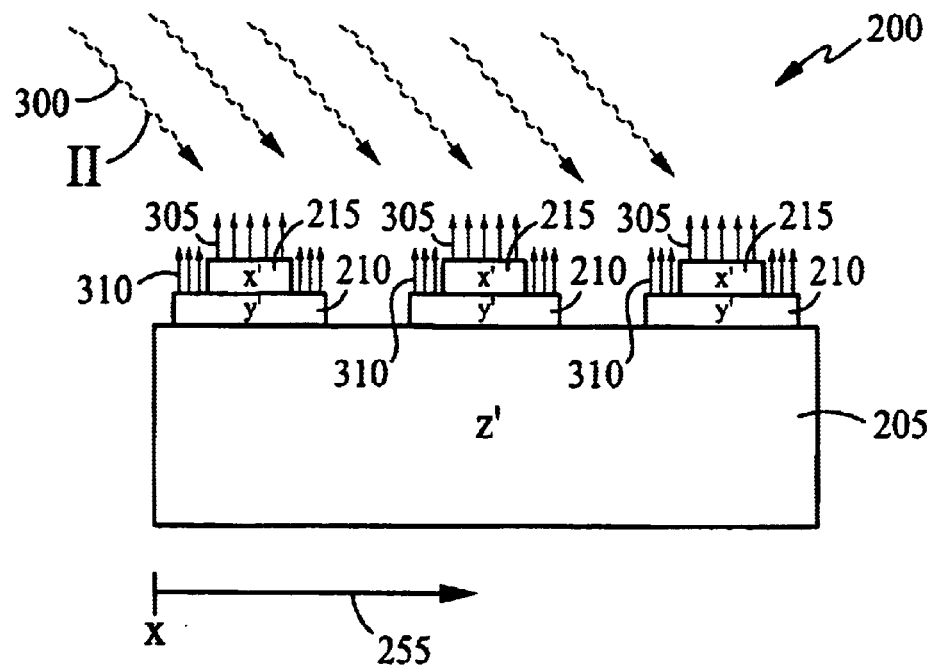
FIGS. 3A and 3B illustrate an example of inspection of a patterned surface (FIG. 3A) and a corresponding photoelectron yield graph (FIG. 3B) when the inspection system employs a light source of higher energy than that of FIGS. 2A and 2B.
Figure 3B:
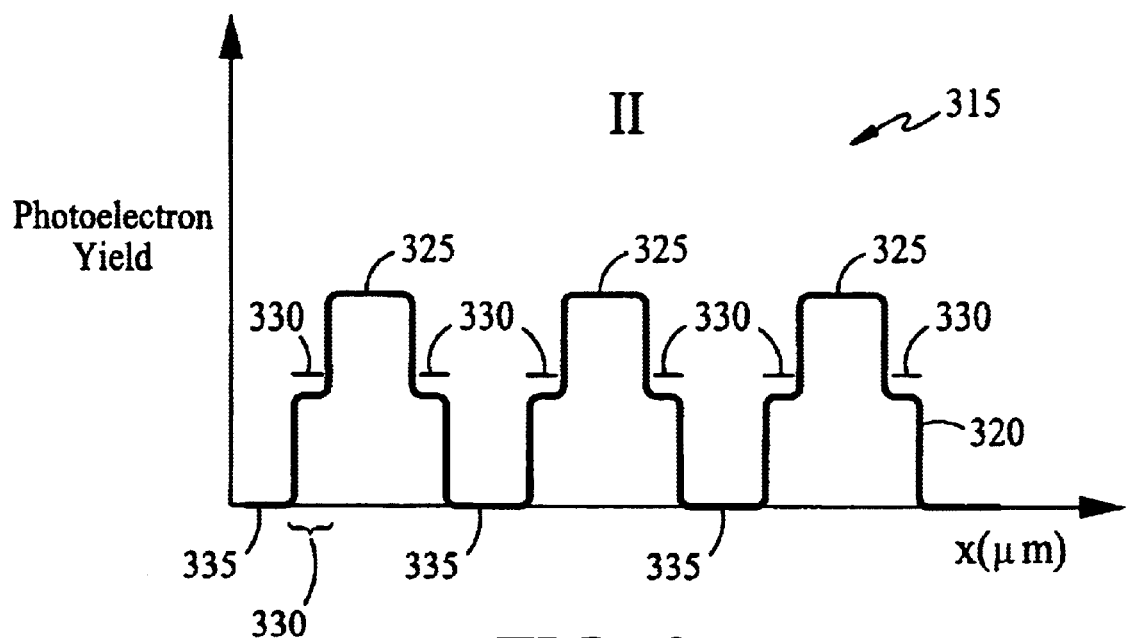

FIGS. 3A and 3B show the inspection of the patterned surface 200 when it is inspected by an inspection system using the light source II. As shown in FIG. 3A, during inspection, photons 300 from light source II are directed at the patterned surface 200. The photons 300 impinge upon the exposed portions of the substrate 205, the patterned layer 210, and the patterned layer 215. The light source II has a higher frequency than light source I and imparts more energy to the patterned surface 200. The photons 300 have enough energy to cause electrons to be emitted from the exposed portions of both the patterned layer 215 and the patterned layer 210, but the photons 300 do not have enough energy to cause electrons to be emitted from the exposed portions of the substrate 205. This is consistent with FIG. 1 in which the photon energy of light source II is greater than both the work function $\Phi x'$ 125 and the work function $\Phi y'$ 130 but less than the work function $\Phi z'$ 135.

The emitted electrons from the exposed portions of the patterned layer 215 and the patterned layer 210 are represented by vertical arrows 305 and 310, respectively. The length of the arrows correlates to the intensity of the photoelectrons emitted from the surface. As shown in FIG. 1, the intensity of the emitted electrons from material x' when exposed to light source II is greater than that when exposed to light source I. Therefore, the arrow 305 is longer than arrow 225.

The amount of emitted electrons that may be collected from the patterned surface 200 along an x-axis 255 is shown in the photoelectron yield graph 315 of FIG. 3B. The yield of photoelectrons emitted from the patterned surface 200 when exposed to light source II is represented by yield curve 320. In this example, the yield curve 320 exhibits peaks 325 that represent the yield of electrons emitted from the exposed portions of the patterned layer 215. The peaks 325 are higher than the peaks 240 because the higher energy of the light source II causes a greater quantity of electrons to be emitted from the patterned layer 215.

The yield curve 320 includes portions 330 that represent the yield of electrons emitted from the exposed portions of the patterned layer 210. The yield curve slopes down steeply from the peaks 325 to the portions 330 at the points on the x-axis corresponding to the boundaries between the exposed portions of the patterned layer 215 and the patterned layer 210. The difference in yield between the peaks 325 and the portions 330 is directly correlated to the image contrast that can be achieved between patterned layer 215 and 210. In particular, the image contrast increases as the yield difference between the peaks 325 and the portions 330 increases. As the image contrast between layers increases, the ability of the system to determine whether an imaged portion belongs to patterned layer 215 or patterned layer 210 also increases.

The yield curve 320 also exhibits troughs 335 at points on the x-axis that correspond to the exposed portions of the substrate 205. The troughs 335 occur because the light source II does not impart enough energy to cause emission of electrons from the substrate 205. Therefore, the yield of electrons collected from the exposed portions of the substrate 205 is negligible.

When imaging the patterned surface 200 using the light source II, the image contrast between the patterned layer 210 and the substrate 205 is related to the difference in yield between the portions 330 and the troughs 335. If the difference is small, the image of the patterned layer 210 is hard to distinguish from the substrate 205. Similarly, the yield difference between the peaks 325 and the troughs 335 is related to the image contrast between the patterned layer 215 and the substrate 205. Again, if the difference is small, the image of the patterned layer 215 is hard to distinguish from that of the substrate 205.

Figure 4:
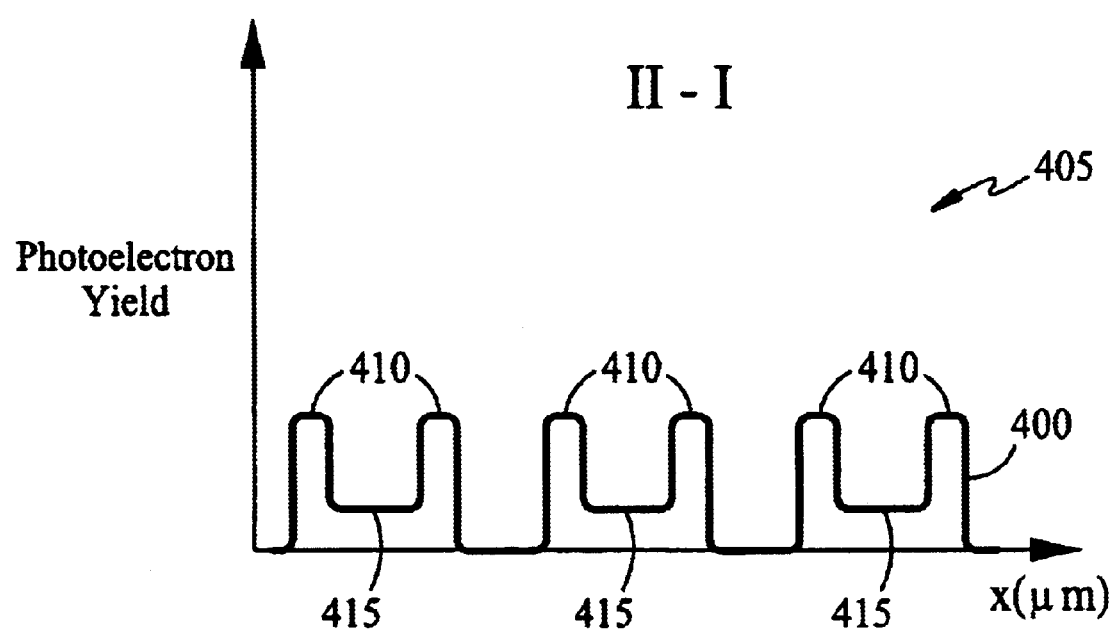
FIG. 4 illustrates a yield graph that is generated by subtraction of the yield graph of FIG. 2B from the yield graph of FIG. 3B.

Image contrast between layers may be improved by illuminating the layers using multiple light sources and storing the yield data of the layers corresponding to each different light source. The yield data corresponding to a given light source may be subtracted from the yield data corresponding to another light source to improve image contrast. For example, patterned layer 210 may be isolated and imaged by subtracting the yield data obtained using light source I from the yield data obtained using light source II. Using the yield graphs 215 and 315, the subtracting of the yield data may be implemented by subtracting the yield curve 235 from the yield curve 320. The result of the subtraction is shown in FIG. 4 as the yield curve 400 of graph 405.

The yield curve 400 has peaks 410 that approximate the yield of the photoelectrons emitted from the patterned surface 210 when exposed to the light source II. The electrons emitted from the patterned surface 215 when exposed to light source II are effectively removed from the image by subtracting the yield curves. However, subtracting the yield curve 235 from yield curve 320 does not entirely eliminate the yield of electrons from patterned layer 215 because there is a higher yield of electrons from the higher energy light source II than from the light source I. As shown in FIG. 4, the troughs 415 represent a greater than zero yield corresponding to the higher yield of electrons from exposed portions of the patterned layer 215. However, normalization of the initial image data to photoemission yield and to light source power may correct for any distortion and maximize image contrast.

Figure 5A:
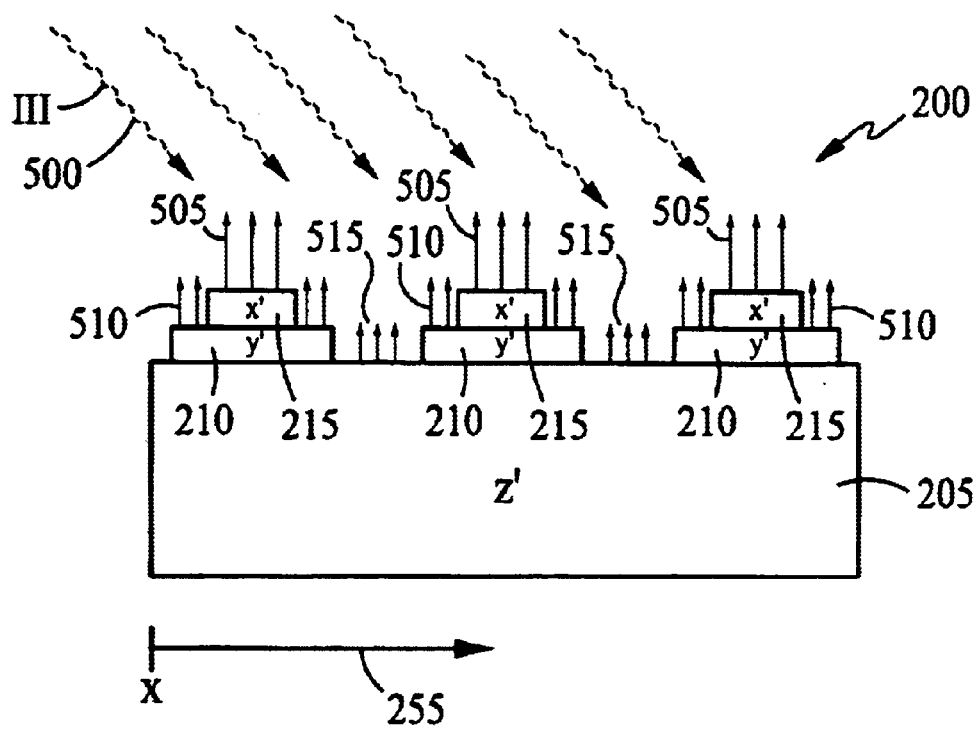
FIGS. 5A and 5B illustrate an example of inspection of a patterned surface (FIG. 5A) and a corresponding photoelectron yield graph (FIG. 5B) when the inspection system employs a light source of higher energy than that of FIGS. 3A and 3B.
Figure 5B:
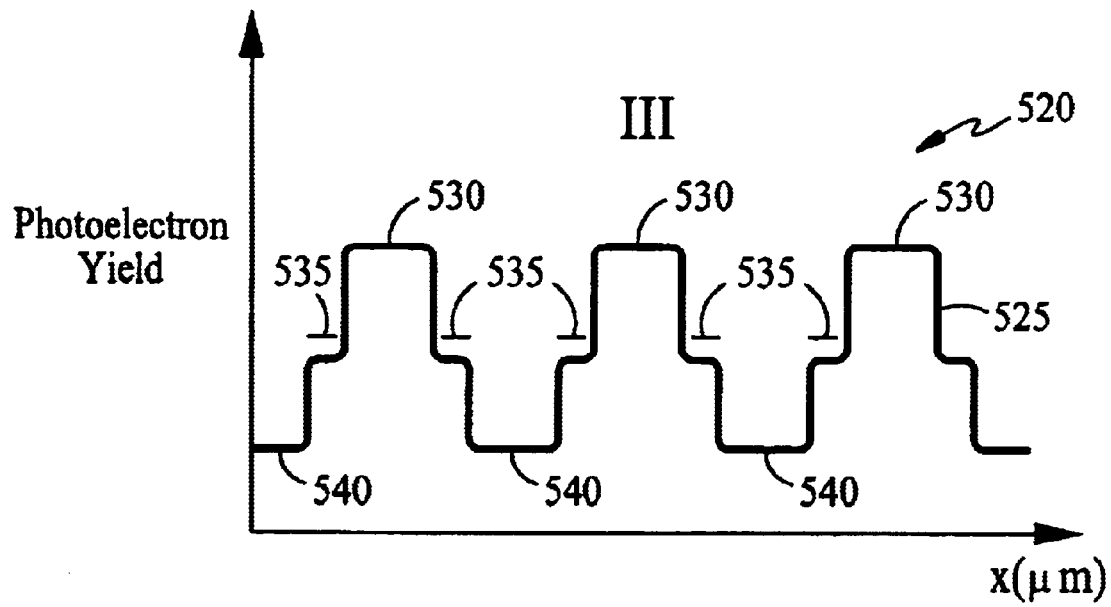

FIGS. 5A and 5B show the patterned surface 200 when it is inspected by an inspection system using light source III. Photons 500 from light source III are directed at the patterned surface 200. The photons 500 impinge upon the exposed portions of the substrate 205, the patterned layer 210, and the patterned layer 215. The light source III has a higher frequency than the two other light sources I and II, and, therefore, imparts the most energy of the three light sources (i.e., I, II, and III) to the patterned surface 200. The photons 500 of light source III have enough energy to cause electrons to be emitted from all three materials x', y', and z'. As a result all exposed portions of the patterned surface 200 emit electrons. This is consistent with FIG. 1 in which the photon energy of light source III is greater than all three work functions $\Phi x'$ 125, $\Phi y'$ 130, and $\Phi z'$ 135.

The emitted electrons from the exposed portions of patterned layer 215, patterned layer 210, and the substrate 205 are represented by vertical arrows 505, 510, and 515, respectively. The lengths of the arrows correlate to the intensity of the photoelectrons emitted from the surfaces. The intensity of photoelectrons emitted from patterned layer 215, patterned layer 210, and substrate 205 correspond to the intensities at 170, 175, and 180 on the graph 120.

The amount of emitted electrons that may be collected from the patterned surface 200 along an x-axis 255 is shown in the photoelectron yield graph 520. The yield of photoelectrons emitted from the patterned surface 200 when exposed to light source III is represented by yield curve 525. In this example, the yield curve 525 exhibits peaks 530 that represent the yield of electrons emitted from the exposed portions of layer 215. The peaks 530 are higher than both the peaks 325 and the peaks 240 because the higher energy of the light source III produces a greater quantity of emitted electrons from the patterned layer 215.

The yield curve 525 also includes portions 535 that represent the yield of electrons emitted from the exposed portions of the patterned layer 210. The yield curve 525 slopes down steeply from the peaks 530 to the portions 535 at the points on the x-axis 255 corresponding to the boundaries between the exposed portions of the patterned layer 215 and the patterned layer 210.

The yield curve 525 also includes troughs 540 that represent the yield of electrons emitted from the exposed portions of the substrate 205. The yield curve 525 slopes down steeply from portions 535 to the troughs 540 at the points on the x-axis 255 corresponding to the boundaries between the exposed portions of the patterned layer 210 and the substrate 205. Though not shown in FIG. 5, if an exposed portion of patterned layer 215 is directly adjacent to an exposed portion of the substrate 205, then the yield curve 525 would slope directly down from a peak 530 to a trough 540.

Image contrast between the layers is related to the difference in yield of emitted electrons between the layers and the substrate. Specifically, a large yield difference between the peaks 530 and the portions 535, and between the peaks 530 and the troughs 540, enables an inspection system to more effectively distinguish the patterned layer 215 from the patterned layer 210 and the substrate 205, respectively. A large yield difference between the portions 535 and the peaks 530 enables the inspection system to more effectively distinguish the patterned layer 210 from the patterned layer 215. Similarly, a large yield difference between the portions 535 and the troughs 540 enables the inspection system to more effectively distinguish the patterned layer 210 from the substrate 205.

As described above, image contrast between layers may be improved by inspecting the layers using multiple light sources, storing the yield data corresponding to each light source, and performing calculations on the yield data. Specifically, an image of the exposed portions of the substrate 205 may be obtained by isolating the yield of emitted electrons from the substrate 205. The yield of emitted electrons from the substrate 205 can be achieved by subtracting the yield data of the patterned surface 200 obtained using light source II from the yield data obtained using light source III.

Using the yield graphs 315 and 520, the yield curve 320 may be subtracted from the yield curve 525 to isolate the yield data corresponding to the electrons from the substrate 205. The yield curve may be corrected to account for the difference in intensity between photoelectrons emitted from materials x' and y' when exposed to light source II and photoelectrons emitted from the same materials when exposed to the higher energy light source III. The corrected yield curve shows the isolated yield of electrons emitted from substrate 205. The corrected yield curve is similar to the yield curve 400 except that the corrected yield curve corresponds to electrons emitted from the substrate 205 rather than the electrons emitted from the patterned layer 210.

A photoelectron emission inspection system can image various layers of a patterned surface by selecting one or more light sources directed at that patterned surface. Depending on the intrinsic properties of the layers of the patterned surface, the light source energy may be chosen to image one or more of the layers. High contrast between layers may be achieved by selecting the light sources such that the photon energy is sufficient to cause only one of the layers to emit electrons (i.e., the photon energy of the light source is greater than the work function of the selected layer material but lower than the work functions of any other layers, e.g., as shown in FIG. 2). High contrast also may be achieved by selecting light sources that maximize the photoelectron intensity difference between multiple layers that are emitting electrons (e.g., as shown in FIGS. 3 and 5). Finally, image contrast may be Manipulated and improved by imaging multiple times using a different light source each time and performing calculations on the yield data collected (e.g., as shown in FIG. 4).

For any given light source, the materials of the layers of a patterned surface may be chosen to optimize imaging (e.g., by providing high contrast between layers). For example, selecting a material for one layer that emits electrons and selecting materials for other layers that do not emit electrons provides optimal imaging of the electron-emitting layer. Additionally, selecting a combination of layer materials to maximize the photoelectron yield difference between the layers also enhances the ability of an inspection system to image the multiple layers.

Figure 6:
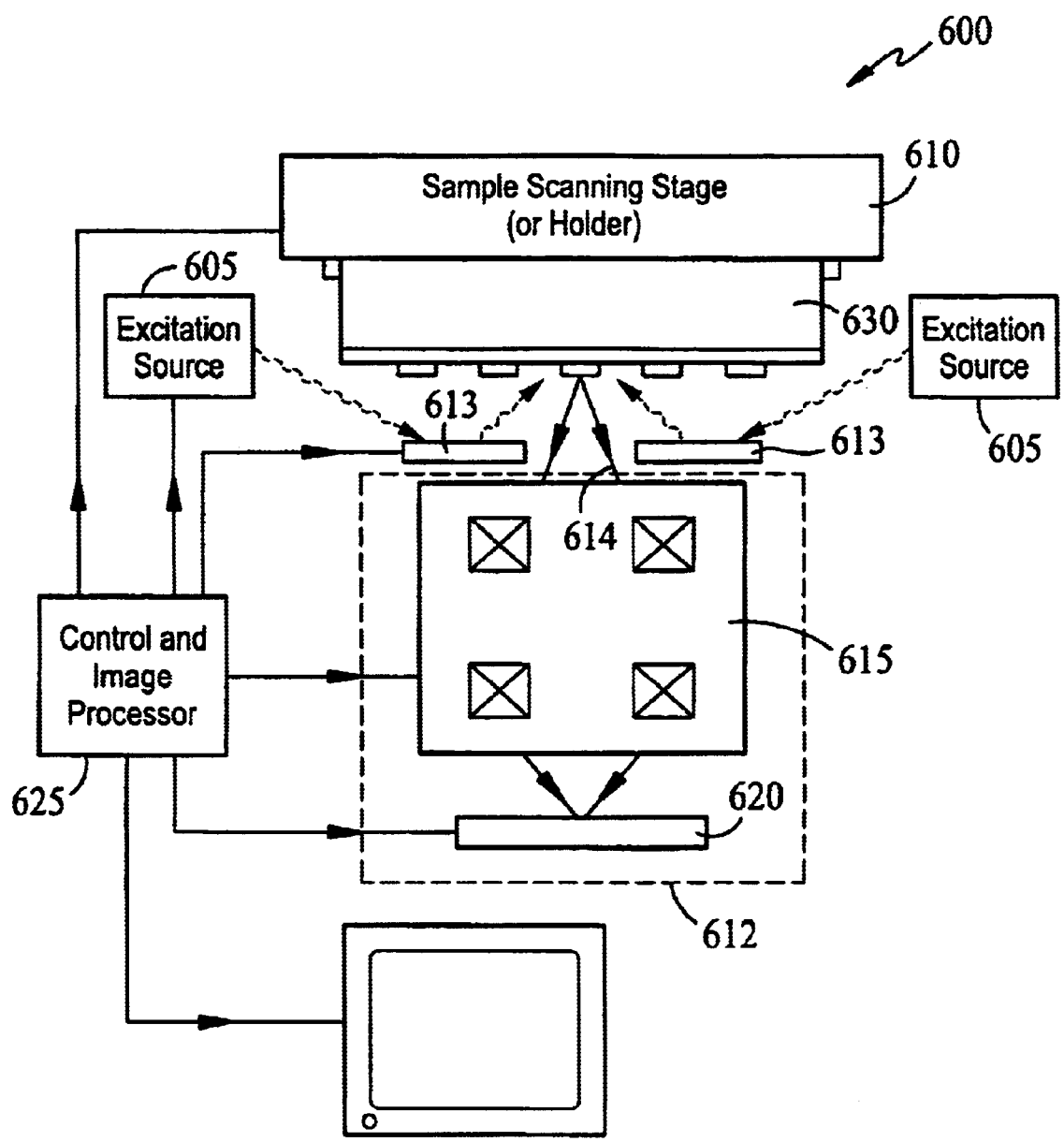
FIG. 6 is a is a block diagram of an example of a photoelectron microscopic inspection system.

Referring to FIG. 6, a photoelectron microscopic inspection system 600 includes an excitation source for photoemission 605, a sample scanning stage or holder 610, an inspection device 612 (including an imaging system 615 and a detection system 620), an extractor 613, a control and image processor 625, and a handling system (not shown). The system 600 may inspect a patterned surface 630 to determine patterns, defects, and irregularities.

The excitation source 605 generates light to which the patterned surface 630 may be exposed. As described above, the excitation source 605 may be selected to provide a suitable wavelength to optimize the imaging of the patterned surface 630 being inspected. The excitation source 605 may be a high intensity light source that,ensures substantial photoelectron generation and provides a strong inspection signal. For example, the excitation source 605 may be a high intensity laser in the UV or DUV range. In one implementation, a 157 nm excimer laser with 10W power and 1–2 kHz repetition rate may be used. The high power of the excitation source 605 allows the photoemission inspection system 600 to generate a stronger inspection signal than is generated by scanning electron microscope (SEM) inspection tools.

The inspection system 600 may use tunable lasers and sum-frequency generation to achieve a wide variety of excitation source frequencies. Image contrast may be improved by the switching between excitation sources 605 of different frequencies to optimize image contrast as described above.

The sample scanning stage or holder 610 guides the patterned surface 630 such that the entire pattern of the surface may be scanned through the field of view of a microscope of the imaging system 615. The field of view of a microscope is the area of a surface visible to a microscope when viewing the surface through the microscope at a given instant of time. The stage or holder 610 should be relatively stable to achieve high spatial resolution.

A laser interferometer may be used to control the motion of the stage or holder 610. During inspection, the stage or holder 610 scan may be synchronized with the detection system 620 (i.e., the stage movement should be coordinated with the detection system so that the detection system keeps track of the location of the surface under the current field of view of the microscope in relation to the rest of the patterned surface 630).

The extractor 613 serves two functions. The first function is to direct light from the excitation source 605 to the patterned surface 630 with the polished surface of extractor 613. The second function is to act as an anode to extract photoelectrons 614 emitted from the surface. The accelerated electrons are imaged by the imaging system 615.

The imaging system 615 may be implemented using a photoemission electron microscope (PEEM). A PEEM is an electrostatic or electromagnetic lens system that is similar to an SEM, with the exception that the collected electrons are photoelectrons emitted from the patterned surface 630 rather than secondary electrons generated, for example, by an electron gun. The PEEM magnifies the surface within the field of view and forms an image for the detection system 620. An electrostatic potential is applied to the patterned surface 630, which acts as the photocathode to extract the emitted photoelectrons.

Once the image is formed with high-energy electrons in the PEEM, the detection system 620 can either detect the electrons directly or may convert the electrons to visible or ultaviolet light prior to detection. To convert the electrons to light, a phosphor or scintillator screen may be used. The detection system 620 may convert the electron or light image to digital form using an image sensor with an array of pixels such as a charged coupled device (CCD). A read-out from the array detector may be digitized, processed, and stored by the detection system 620.

The image and control processor 625 may control the sample scan, the pattern alignment, the excitation source, and the imaging and detection systems. The image and control processor 625 also may be used to analyze patterns, irregularities, and defects in the patterned surface 630.

In one implementation, pattern inspection may be used to identify defects. A defect may be defined as any deviation or imperfection from a design, particularly one that reduces, diminishes, or impairs the operation of a patterned device. With this definition, one difference between pattern inspection and simple microscopy is that the image of the patterned device must be compared to that of a defect-free design. Such a comparison is usually carried out in either a die-to-die or a die-to-database mode. The die-to-die mode compares images of adjacent dies. The die-to-database mode compares the actual pattern to calculated images of a defect-free pattern stored, for example, in a database. If the deviation between the adjacent dies or between a given die and the calculated images falls within an acceptable range, then the die passes the inspection and is considered functional. If, on the other hand, the deviation exceeds the acceptable range, then the die fails the inspection and may be removed or excluded from further processing.

The processor 625 (or another processor) may be used to carry out analysis of the patterned surface. For example, the processor may analyze the patterned surface in the die-to-die mode or the die-to-database mode. Image processing may be carried out using the images created by the inspection system. The processor 625 also may be used to carry out the calculations, such as, for example, image normalization and yield curve subtraction.

The inspection system 600 also may include a handling system (not shown) to keep the samples clean and to keep them free from added contamination during inspection. The handling system is particularly important for mask inspection. The handling system may be an automated system with robotic loading and unloading mechanisms.

Figure 7:
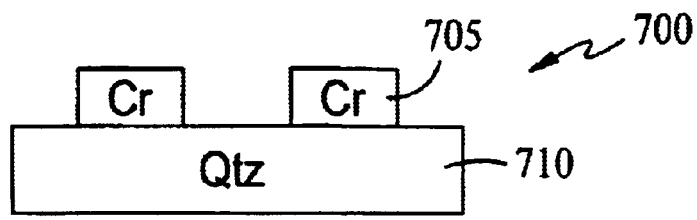
FIG. 7 is a cross-sectional view of a chrome on glass binary mask.
Figure 8:
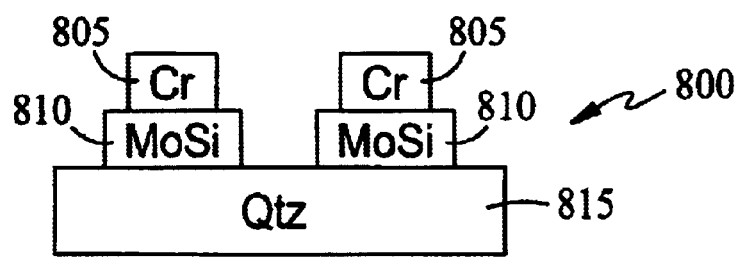
FIG. 8 is a cross-sectional view of a ternary phase shift mask with MoSi as the phase shifter.
Figure 9:
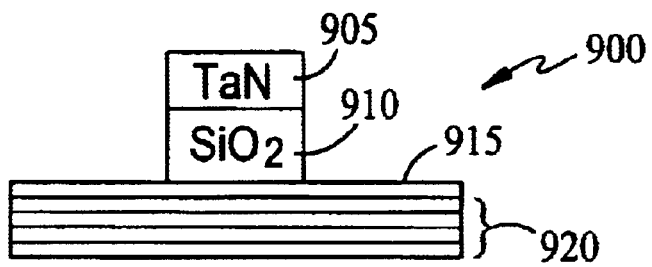
FIG. 9 is a cross-sectional view of an EUV mask with TaN as the absorber.

Examples of patterned surface material and light combinations that may be inspected using a photoelectron microscopic inspection system 600 include a chromium (chrome) on glass binary mask 700 as shown in FIG. 7, a ternary phase shift mask 800 with molybdenum silicon (MoSi) as the phase shifter as shown in FIG. 8, and an EUV mask 900 with tantalum nitride (TaN) as the absorber as shown in FIG. 9. These examples are illustrative and are not meant to be limiting as to light sources and patterned layer material combinations.

Referring to FIG. 7, a chrome on glass binary mask 700 includes a patterned chrome layer 705 positioned on top of a quartz (SiO2) substrate 710. A 248 nm KrF laser may be used as the light source to excite photoemission from the chrome and obtain image contrast. The following table provides a summary of this material and light combination:

| Light Source | | Material | Work function |
|---|---|---|---|
| I | λ = 248 nm (5.0 eV) | X' | Cr | ΦCr = 4.5 eV |
| II | N/A | Y' | SiO2 | transparent |
| III | N/A | Z' | N/A | N/A |
| IV | N/A | X" | N/A | N/A |

Note that the roman numerals I, II, III, and IV and the letters X', Y', Z', and X" are used to label the light sources and the materials in a manner similar to that used in the description with respect to the patterned surface 200 and FIGS. 1—5. Note also that N/A stands for not applicable.

Referring to FIG. 8, the ternary phase shift mask 800 with MoSi as the phase shifter includes a chrome patterned layer 805, a MoSi patterned layer 810, and a quartz (SiO2) substrate 815. A 310 nm wavelength light source may be used to cause only the exposed portions of the MoSi patterned layer 810 to emit photoelectrons. The 310 nm light source may be obtained by using frequency doubling on an Ar/Kr mixed gas ion laser (tunable at 477 nm to 656 nm). By using a 248 nm laser, both the exposed portions of the chrome patterned layer 805 and the MoSi patterned layer 810 emit electrons. The chrome patterned layer 805 may be isolated and imaged in a manner similar to that described in conjunction with FIG. 4 by subtracting the normalized yield data of the MoSi patterned layer 810 obtained using the 310 nm light source from the normalized yield data of the chrome patterned layer 805 and MoSi patterned layer 810 obtained using the 248 nm laser. The following table provides a summary of this material and light combination:

| Light Source | | Material | Work function |
|---|---|---|---|
| I | λ = 310 nm (4 eV) | X' | Cr | ΦCr = 4.5 eV |
| II | λ = 248 nm | Y' | MoSi | ΦMoSi = 3.87 eV |
| III | N/A | Z' | SiO2 | transparent |
| IV | N/A | X" | N/A | N/A |

Referring to FIG. 9, an EUV mask 900 with TaN as the absorber includes a TaN patterned layer 905, an SiO2 buffer layer 910, a Si capping layer 915, and a stack of Mo—Si multilayers 920. The process used to create this mask involves patterning the TaN using an SiO2 buffer layer and requires an initial inspection of the TaN patterned layer 905 prior to etching the SiO2 layer.

Figure 10:
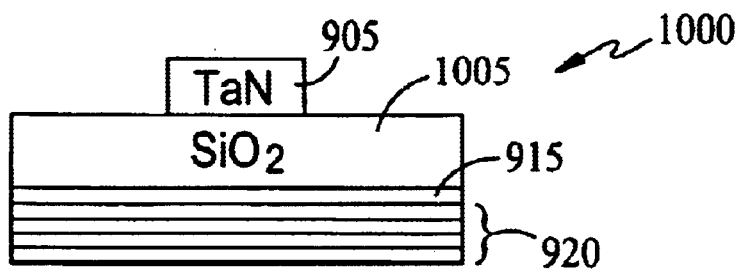
FIG. 10 is a cross-sectional view of the EUV mask of FIG. 9 prior to etching.

FIG. 10 shows the patterned surface 1000 prior to etching. An initial inspection of the patterned surface 1000 is possible by using a 266 nm laser which causes only the TaN to photoemit electrons. The 266 nm laser does not provide enough photon energy to cause an unetched SiO2 layer 1005 to absorb the light and photoemit. Once the SiO2 buffer layer is etched, the final EUV mask 900 may be inspected using the same 266 nm laser. Only the TaN will photoemit because the 266 nm laser does not provide enough photon energy to cause the silicon capping layer 915 to photoemit. The following table provides a summary of this material and light combination:

| Light Source | | Material | | Work function |
|---|---|---|---|---|
| I | λ = 266 nm (4.7 eV) | X' | TaN | ΦTaN = 4.1 eV |
| II | N/A | Y' | SiO2 | transparent |
| III | N/A | Z' | Si | ΦSi = 5.2 eV |
| IV | N/A | X" | MoSi | ΦMoSi = 3.87 eV |

The photoemission microscopy inspection system 600 may be used for general inspection of surface patterns and microstructures of different materials. For example, such a system is particularly useful for mask defect inspection. Masks are generally patterned with metals or metal-like materials (e.g., Cr, TaN, Ti, and W) on a quartz or a dielectric substrate and photoemissions from these different materials provides good contrast. Binary chrome-on-glass, phase shift, extreme ultraviolet, electron projection lithography, ion projection lithography, and scattering with angular limitation projection electron beam lithography (SCALPEL) masks may be imaged and inspected.

The inspection system 600 also may be used for wafer pattern defect inspections. Photoemission from metals on the wafer (such as Cu, W, Ti, or Al) oxides, and nitrides are very different, and therefore, good image contrast for defect or structural inspection on patterned wafers in a variety of processing steps may be achieved.

The inspection system 600 also may be used to inspect microelectrical mechanical systems (MEMS) and nanostructures as well as carbon nanotubes. Carbon nanotubes may be used in a variety of applications when put into certain patterns on different substrates. Photoelectron image contrast is good because carbon has a low photoelectron yield as compared to most metal and semiconductor materials.

The photoelectron microscopic inspection system 600 offers the ability to resolve feature sizes smaller than those normally resolvable by optical inspection systems at a speed comparable to that of an optical system. In particular, the use of electrons to create the image signal allows the photoelectron inspection system 600 to resolve smaller feature sizes than optical inspection systems. In addition, the photoelectron microscopic inspection system 600 does not suffer from the very low pixel-by-pixel scan speed, for example, of scanning electron inspection technologies.

A number of exemplary implementations have been described. Nevertheless, it will be understood that various modifications may be made. For example, advantageous results may be achieved if the steps of disclosed techniques are performed in a different order and/or if components in a disclosed architecture, devices, systems, or circuits are combined in a different manner and/or replaced or supplemented by other components. Accordingly, other implementations are within the scope of the following claims.

What is claimed is:

1. A method of inspecting a patterned surface, the method comprising:
    selecting two different metal or metal-like materials, each material having a distinct work function or transparency;
    selecting a first light source having an energy level that produces a difference in yield of photoelectrons emitted from the two materials when applied to the two materials;
    applying light from the first light source to a patterned surface including at least one region of the first material and at least one region of the second material;
    detecting the emission of photoelectrons from the patterned surface; and
    distinguishing between the two materials on the patterned surface based on the detected photoelectron emission.

2. The method of claim 1 further comprising forming an image of the patterned surface based on the emission of photoelectrons from the patterned surface.

3. The method of claim 2 wherein selecting the two materials includes selecting the two materials to provide high contrast between the two materials in the image.

4. The method of claim 1 further comprising detecting defects in the patterned surface based on the detected photoelectron emissions.

5. The method of claim 1 further comprising collecting and storing a first set of yield data for the emission of photoelectrons from the patterned surface.

6. The method of claim 5 further comprising:
    selecting a second light source having an energy level that produces a difference in yield of photoelectrons emitted from the two materials;
    applying light from the second light source to the patterned surface;
    detecting a second emission of photoelectrons from the patterned surface in response to the light from the second light source; and
    distinguishing between the two materials on the patterned surface based on the first set of yield data and the second emission of photoelectrons from the patterned surface.

7. The method of claim 6 wherein selecting the second light source includes selecting a light source that has a frequency different from the first light source.

8. The method of claim 6 further comprising collecting and storing a second set of yield data for the second emission of photoelectrons from the patterned surface.

9. The method of claim 8 further comprising generating a third set of yield data based on calculations performed on the first set of yield data and the second set of yield data.

10. The method of claim 9 wherein distinguishing between the two materials on the patterned surface includes inspecting an image of the patterned surface generated based on the third set of yield data.

11. The method of claim 9 wherein generating the third set of yield data includes subtracting the first set of yield data from the second set of yield data to improve image contrast.

12. The method of claim 9 wherein generating the third set of yield data includes subtracting the second set of yield data from the first set of yield data to improve image contrast.

13. The method of claim 9 wherein generating the third set of yield data includes normalizing yield data to photoemission yield or light source power.

14. A method of detecting features of a patterned surface, the method comprising:
    selecting two different metal or metal-like materials, each material having a distinct work function or transparency to provide a difference in yield of photoelectrons emitted from the two materials in response to light applied to the two materials;
    applying light from a first light source to a patterned surface including at least one region of the first material and at least one region of the second material; and
    detecting features of the patterned surface and distinguishing between the two materials on the patterned surface based on the photoelectron emission of the two materials.

15. The method of claim 14 further comprising forming an image of the patterned surface based on the photoelectron emission of the two materials.

16. The method of claim 14 further comprising detecting defects in the patterned surface based on the photoelectron emission of the two materials.

17. The method of claim 14 wherein selecting the two materials includes selecting the two materials to provide high contrast between the two materials in the image.

18. The method of claim 14 further comprising collecting and storing a first set of yield data for the photoelectron emission of the two materials.

19. The method of claim 18 further comprising: applying light from a second light source to the patterned surface; and
detecting features of the patterned surface and distinguishing between the two materials based on the first set of yield data and a second photoelectron emission of the two materials in response to the light from the second light source.

20. The method of claim 19 further comprising selecting the second light source by selecting a light source that produces light having a frequency different than light produced by the first light source.

21. The method of claim 19 further comprising collecting and storing a second set of yield data for the second photoelectron emission of the two materials.

22. The method of claim 21 further comprising generating a third set of yield data based on calculations performed on the first set of yield data and the second set of yield data.

23. The method of claim 22 wherein detecting features of the patterned surface includes detecting features of an image of the patterned surface generated based on the third set of yield data.

24. The method of claim 22 wherein generating the third set of yield data includes subtracting the first set of yield data from the second set of yield data to improve image contrast.

25. The method of claim 22 wherein generating the third set of yield data includes subtracting the second set of yield data from the first set of yield data to improve image contrast.

26. The method of claim 22 wherein generating the third set of yield data includes normalizing yield data to photoemission yield or light power.

27. A method of detecting features of a patterned surface, the method comprising:
providing a patterned surface including two different metal or metal-like materials, each material having a distinct work function or transparency to provide a difference in yield of photoelectrons from the two materials in response to a light applied to the two materials;
selecting a first light source that produces light having an energy level that results in a difference in yield of photoelectrons emitted from the two materials when applied to the two materials;
applying light from the first light source to the patterned surface including at least one region of the first material and at least one region of the second material; and
detecting features of the patterned surface and distinguishing between the two materials on the patterned surface based on the photoelectron emission of the two materials.

28. The method of claim 27 further comprising forming an image of the patterned surface based on the photoelectron emission of the two materials.

29. The method of claim 27 further comprising detecting defects in the patterned surface based on the photoelectron emission of the two materials.

30. The method of claim 27 further comprising collecting and storing a first set of yield data for the emission of photoelectrons from the patterned surface.

31. The method of claim 30 further comprising:
selecting a second light source that produces light having an energy level that results in a difference in yield of photoelectrons emitted from the two materials when applied to the two materials;
applying light from the second light source to the patterned surface; and
detecting features of the patterned surface based on the first set of yield data and a second photoelectron emission of the two materials in response to the light produced by the second light source.

32. The method of claim 31 wherein selecting the second light source includes selecting a light source that produces light having a frequency different than light produced by the first light source.

33. The method of claim 31 further comprising collecting and storing a second set of yield data for the second photoelectron emission of the two materials.

34. The method of claim 33 further comprising generating a third set of yield data based on calculations performed on the first set of yield data and the second set of yield data.

35. The method of claim 34 wherein detecting features of the patterned surface includes detecting features of an image of the patterned surface generated based on the third set of yield data.

36. The method of claim 34 wherein generating the third set of yield data includes subtracting the first set of yield data from the second set of yield data to improve image contrast.

37. The method of claim 34 wherein generating the third set of yield data includes subtracting the second set of yield data from the first set of yield data to improve image contrast.

38. The method of claim 34 wherein generating the third set of data includes normalizing yield data to photoemission yield or light power.

39. An inspection system comprising:
an excitation source for photoemission;
a holder to secure a patterned surface including two different metal or metal-like materials, each material having a distinct work function;
an inspection device to detect the emission of photoelectrons from the two materials when the excitation source is applied to the two materials;
an extractor; and
a processor to analyze the detected photoelectron emission and to distinguish between the two materials.

40. The system of claim 39 wherein the inspection device is a photoelectron emission microscope.

41. The system of claim 39 wherein the inspection device includes an electrostatic lens system.

42. The system of claim 39 wherein the inspection device includes an electromagnetic lens system.

43. The system of claim 39 wherein the inspection device includes a detection system that converts collected photoelectrons to a digital image.

44. The system of claim 43 wherein the detection system includes a phosphor or scintillator screen.

45. The system of claim 43 wherein the detection system includes a pixel array detector.

46. The system of claim 45 wherein the pixel array detector is a charge-coupled device pixel array.

47. The system of claim 39 wherein the processor is programmed to form an image of the patterned surface.

48. The system of claim 39 wherein the processor is programmed to analyze patterns, irregularities, or defects in the patterned surface.

49. The system of claim 39 wherein the processor is programmed to carry out die-to-die comparisons of patterns.

50. The system of claim 39 wherein the processor is programmed to carry out die-to-database comparisons of patterns.

51. The system of claim 39 wherein the frequency of the excitation source may be varied.

52. The system of claim 39 further comprising a second excitation source having a frequency different than the excitation source.

53. The system of claim 39 wherein the excitation source is a high intensity laser in the ultraviolet or deep ultraviolet range.

54. The system of claim 39 wherein the excitation source is a tunable laser.

55. The system of claim 39 wherein a frequency of the excitation source is achieved through sum-frequency generation.

56. The system of claim 39 further comprising a storage to store yield data on the emission of photoelectrons from the patterned surface.

57. The system of claim 56 wherein the processor is programmed to perform calculations on yield data to improve image contrast of an image formed based on yield data of the patterned surface.

58. The system of claim 56 wherein the processor is programmed to subtract a first set of yield data generated by photoelectron emission of the two materials in response to a first excitation source from a second set of yield data generated by a second photoelectron emission of the two materials in response to a second excitation source to generate a third set of yield data that improves image contrast of an image of the patterned surface.

59. The system of claim 56 wherein the processor is programmed to normalize yield data to photoemission yield or light power.

60. The system of claim 39 wherein the extractor directs light from the excitation source to the patterned surface and acts as an anode to extract photoelectrons emitted from the patterned surface.

61. A method of inspecting a patterned surface, the method comprising:
  selecting two materials, each material having a distinct work function or transparency;
  selecting a first light source having an energy level that produces a difference in yield of photoelectrons emitted from the two materials when applied to the two materials;
  applying light from the first light source to a patterned surface including at least one region of the first material and at least one region of the second material;
  detecting the emission of photoelectrons from the patterned surface;
  selecting a second light source having an energy level that produces a difference in yield of photoelectrons emitted from the two materials;
  applying light from the second light source to the patterned surface;
  detecting a second emission of photoelectrons from the patterned surface in response to the light from the second light source; and
  distinguishing between the two materials on the patterned surface based on the first set of yield data and the second emission of photoelectrons from the patterned surface.

62. The method of claim 61 wherein selecting the second light source includes selecting a light source that has a frequency different from the first light source.

63. The method of claim 61 further comprising collecting and storing a second set of yield data for the second emission of photoelectrons from the patterned surface.

64. The method of claim 63 further comprising generating a third set of yield data based on calculations performed on the first set of yield data and the second set of yield data.

65. The method of claim 64 wherein distinguishing between the two materials includes inspecting an image of the patterned surface generated based on the third set of yield data.

66. The method of claim 64 wherein generating the third set of yield data includes subtracting the first set of yield data from the second set of yield data to improve image contrast.

67. The method of claim 64 wherein generating the third set of yield data includes subtracting the second set of yield data from the first set of yield data to improve image contrast.

68. The method of claim 64 wherein generating the third set of yield data includes normalizing yield data to photoemission yield or light source power.

69. A method of detecting features of a patterned surface, the method comprising:
  selecting two different materials, each material having a distinct work function or transparency to provide a difference in yield of photoelectrons emitted from the two materials in response to light applied to the two materials;
  applying light from a first light source to a patterned surface including at least one region of the first material and at least one region of the second material;
  collecting and storing a first set of yield data for the photoelectron emission of the two materials;
  applying light from a second light source to the patterned surface; and
  detecting features of the patterned surface and distinguishing between the two materials on the patterned surface based on the first set of yield data and a second photoelectron emission of the two materials in response to the light from the second light source.

70. The method of claim 69 further comprising selecting the second light source by selecting a light source that produces light having a frequency different than light produced by the first light source.

71. The method of claim 69 further comprising collecting and storing a second set of yield data for the second photoelectron emission of the two materials.

72. The method of claim 71 further comprising generating a third set of yield data based on calculations performed on the first set of yield data and the second set of yield data.

73. The method of claim 72 wherein detecting features of the patterned surface includes detecting features of an image of the patterned surface generated based on the third set of yield data.

74. The method of claim 72 wherein generating the third set of yield data includes subtracting the first set of yield data from the second set of yield data to improve image contrast.

75. The method of claim 72 wherein generating the third set of yield data includes subtracting the second set of yield data from the first set of yield data to improve image contrast.

76. The method of claim 72 wherein generating the third set of yield data includes normalizing yield data to photoemission yield or light power.

77. A method of detecting features of a patterned surface, the method comprising:
  providing a patterned surface including two different materials, each material having a distinct work function or transparency to provide a difference in yield of photoelectrons from the two materials in response to a light applied to the two materials;

selecting a first light source that produces light having an energy level that results in a difference in yield of photoelectrons emitted from the two materials when applied to the two materials;

applying light from the first light source to the patterned surface including at least one region of the first material and at least one region of the second material;

collecting and storing a first set of yield data for the emission of photoelectrons from the patterned surface;

selecting a second light source that produces light having an energy level that results in a difference in yield of photoelectrons emitted from the two materials when applied to the two materials;

applying light from the second light source to the patterned surface; and detecting features of the patterned surface and distinguishing between the two materials based on the first set of yield data and a second photoelectron emission of the two materials in response to the light produced by the second light source.

78. The method of claim 77 wherein selecting the second light source includes selecting a light source that produces light having a frequency different than light produced by the first light source.

79. The method of claim 77 further comprising collecting and storing a second set of yield data for the second photoelectron emission of the two materials.

80. The method of claim 79 further comprising generating a third set of yield data based on calculations performed on the first set of yield data and the second set of yield data.

81. The method of claim 80 wherein detecting features of the patterned surface includes detecting features of an image of the patterned surface generated based on the third set of yield data.

82. The method of claim 80 wherein generating the third set of yield data includes subtracting the first set of yield data from the second set of yield data to improve image contrast.

83. The method of claim 80 wherein generating the third set of yield data includes subtracting the second set of yield data from the first set of yield data to improve image contrast.

84. The method of claim 80 wherein generating the third set of data includes normalizing yield data to photoemission yield or light power.

85. An inspection system comprising:

an excitation source for photoemission;

a holder to secure a patterned surface including two materials, each material having a distinct work function;

an inspection device to detect the emission of photoelectrons from the two materials when the excitation source is applied to the two materials;

an extractor;

a processor to analyze the detected photoelectron emission and to inspect the patterned surface; and a storage to store yield data on the emission of photoelectrons from the patterned surface, wherein the processor is programmed to subtract a first set of yield data generated by photoelectron emission of the two materials in response to a first excitation source from a second set of yield data generated by a second photoelectron emission of the two materials in response to a second excitation source to generate a third set of yield data that improves image contrast of an image of the patterned surface.

* * * * *